United States Patent [19]
Hirata et al.

[11] 4,343,943
[45] Aug. 10, 1982

[54] CEPHALOSPORIN ANALOGS

[75] Inventors: Tadashi Hirata, Yokohama; Hiromitsu Saito; Nobuhiro Nakamizo, both of Machida, all of Japan

[73] Assignee: Kyowa Hakko Kogyo Co., Ltd., Tokyo, Japan

[21] Appl. No.: 51,758

[22] Filed: Jun. 25, 1979

[30] Foreign Application Priority Data

Jun. 24, 1978 [JP] Japan .................................. 53-7690

[51] Int. Cl.$^3$ .......................................... C07D 211/80
[52] U.S. Cl. .................................... 546/183; 424/256; 424/265
[58] Field of Search ...................... 260/245.2; 546/183; 424/267, 256, 265

[56] References Cited

U.S. PATENT DOCUMENTS 4,011,216  3/1977  Menalo et al. .................. 260/244 R
4,278,793  7/1981  Durcheimer et al. ................ 544/21

FOREIGN PATENT DOCUMENTS 252443  12/1975  Fed. Rep. of Germany .

OTHER PUBLICATIONS

Guthikonda et al., JACS. 7584–7585 (1974).
Cams et al., JACS. 96, 7582–7583 (1974).

Primary Examiner—Nicholas S. Rizzo
Attorney, Agent, or Firm—Fitzpatrick, Cella, Harper & Scinto

[57] ABSTRACT

Novel cephalosporin analogs and intermediates therefor are useful as antibiotics. Methods for producing the compounds are provided.

33 Claims, No Drawings

CEPHALOSPORIN ANALOGS

CROSS REFERENCE TO RELATED APPLICATIONS

This application is related to commonly assigned copending application Ser. No. 023,645 filed Mar. 23, 1979 now U.S. Pat. No. 4,291,164 and Ser. No. 023,646, filed Mar. 23, 1979, now abandoned.

BACKGROUND OF THE INVENTION

1. Field of the Invention

This invention relates to cephalosporin analogs. In particular it relates to cephalosporin analogs having a dihydropyridine ring.

2. Description of Prior Art

Cephalosporins are valuable antibiotics. However, microorganisms, in time, develop strains which are immune to existing antibiotics. Accordingly, new antibiotics will be required with high antibacterial activity.

Cephalosporin analogs have previously been developed where a carbon atom is substituted for the sulfur atom in the dihydrothiazine ring of the cephalosporanic acid ring system. Such compounds are known as carbacephems. In the Journal of the American Chemical Society, 96, 7584 (1974) and J. Med. Chem., 20, 551 (1977), carbacephems having substituted methylene groups at the C-3 position have been proposed, such as $(\pm)$-1-carbacephalothin [$(\pm)$-7$\beta$-(2-thienyl)acetamido-1-methylenedethiacephalosporanic acid].

In commonly assigned, copending application Ser. Nos. 023,645 and 023,646, carbacephems having a hydrogen atom at the C-3 position have been disclosed.

It has now been discovered that novel carbacephems can be prepared having a dihydropyridine ring in place of the tetrahydropyridine ring of the carbacephems referred to in the J.A.C.S. article, Vol. 96, 7584 (1974).

SUMMARY OF THE INVENTION

In accordance with the present invention, cephalosporin analogs are synthesized. The numbering system shown in the following formula is used hereinafter.

Broadly, the present invention relates to cephalosporin analogs represented by the formula:

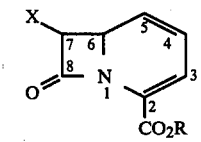
[I]

wherein X represents an amino group, azido group or a protected amino group and R represents a hydrogen atom or a substituted or unsubstituted alkyl, aryl, aralkyl or silyl group.

The present invention also includes the cephalosporin analogs represented by the following general formula (A-I) and derivatives thereof:

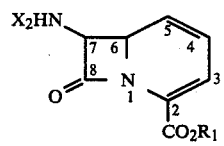
[A-I]

wherein $X_2$ represents an acyl group and $R_1$ represents a hydrogen atom or a protecting group for a carboxylic acid.

The invention also includes a process for making the compounds of the general formula [A-I] by acylating an intermediate represented by general formula [Ib].

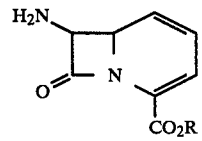

Included in the composition of matter aspect of the invention are the salts of the compounds defined above.

The invention also pertains to the processes for the synthetic production of the cephalosporin analogs of the invention.

DESCRIPTION OF THE INVENTION

This invention relates to cephalosporin analogs represented by the general formula [I]

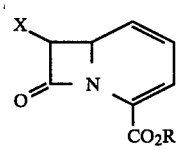

wherein X represents an amino group, azido group or protected amino group and R represents a hydrogen atom or a substituted or unsubstituted alkyl, aryl, aralkyl or silyl group.

As an ester represented by $—CO_2R_1$, an ester generally employed in the field of the synthetic chemistry of penicillins or cephalosporins is suitable. The ester is preferably selected from those groups easily converted to a carboxy group without decomposition of substituents and functional groups of carbacephems under suitable conditions. In the general formula [I], R is preferably an alkyl group having 1 to 5 carbon atoms such as a methyl group, ethyl group, n-propyl group, isopropyl group, n-butyl group, isobutyl group, t-butyl group, and the like; a halogenated alkyl group having 1 to 5 carbon atoms such as a chloromethyl group, 2,2,2-trichloroethyl group, 2,2,2-trifluoroethyl group, etc.; an arylmethyl group having 7 to 20 carbon atoms such as a benzyl group, diphenylmethyl group, triphenylmethyl group, etc.; an arylmethyl group having 7 to 20 carbon atoms and having a methoxy group, nitro group, etc. on the phenyl ring and a substituted silyl group, such as trimethylsilyl group, triphenylsilyl group and the like.

Further, an ester group enzymatically or nonenzymatically convertible in vivo to a carboxyl group, for example, an ester group having as R; a group represented by the general formula

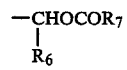
—CHOCOR$_7$
|
R$_6$ (wherein $R_6$ is hydrogen atom or a lower alkyl group, $R_7$ is a lower alkyl group, a lower alkoxy group or a phenyl group) or a group represented by (wherein $R_3$ is a hydrogen atom, a methyl group or a methoxy group) is also preferred.

As the protected amino group X, those protected with conventional amino-protecting groups, such as phthalylimino group, carbobenzoxyamino group, trityl amino group, and the like (J. F. W. McOmie, Protective Group in Organic Chemistry, page 43, 1973) are appropriate.

Compounds of the present invention represented by the general formula [I] include all stereoisomers at the 6 and 7 positions.

As used hereinafter, compounds represented by the general formula [I], [II], etc., are identified as Compound [I], Compound [II], etc., respectively.

Compound [I] can be produced according to Processes I to III set forth below.

(1) Process I

Compound [Ia] represented by the general formula [I] wherein X is an azido group or a protected amino group is prepared according to Flow Sheet [I].

Flow Sheet [I]

wherein $X_1$ represents an azido group, a protected amino group, R has the same significance as defined above, $R_4$ represents a lower alkyl group, an aryl group or an aralkyl group, and Y represents a sulfur atom or a selenium atom.

The reaction is carried out at a temperature of 0° to 200° C., generally 30° to 150° C., with or without a solvent depending on the groups selected as $R_4$ and Y.

As the solvent, organic solvents such as hydrocarbons, halogenated hydrocarbons, ethers, esters, amides, sulfoxides, and the like are appropriate. Toluene or carbon tetrachloride is preferable.

Compound [II], the starting compound, is disclosed in Japanese Patent Application No. 34696/78 and a method for preparing the compound is explained in detail therein. In addition, the preparation of Compound II is set forth in copending application Ser. No. 023,645, filed 23 March 1979, the procedure being set forth on pages 21-28 and said application being incorporated herein by reference.

(2) Process II

Compound [Ib] represented by the general formula [I], wherein X is an amino group, is prepared according to Flow Sheet [II]

Flow Sheet [II]

wherein $X_1$ and R have the same significance as defined above.

When $X_1$ is an azido group, then a catalytic reduction or a method wherein hydrogen sulfide is treated in the presence of a base is preferably employed to convert the azido to an amino group.

As a catalyst for the catalytic reduction, palladium-carbon, Raney nickel, platinum catalyst, and the like are employed. The reaction is carried out at room temperature or under heating up to 100° C. in a solvent generally employed in catalytic reduction, such as water, an alcohol, an ether, acetic acid, or the like.

When R is benzyl or a substituted arylmethyl group, such as p-methoxybenzyl, p-nitrobenzyl, benzhydryl, trityl or the like, then the group $CO_2R$ may be converted to $CO_2H$.

In the reduction step using hydrogen sulfide, the base may be triethylamine, pyridine and the like.

When $X_1$ is a protected amino group, Compound [Ib] is obtained by eliminating the amino protecting group according to a conventional elimination method, for example, the method disclosed in J. F. W. McOmie, Protective Group in Organic Chemistry, page 43, 1973. An exemplary procedure for eliminating the amino protecting group is described on pages 32-34 of said application Ser. No. 023,645.

(3) Process III

Compound [Ic] represented by the general formula [I] wherein R is a hydrogen atom is prepared according to Flow Sheet [III].

Flow Sheet III wherein X has the same significance as defined above and $R_5$ has the same definition as R except for excluding hydrogen atom.

The reaction is carried out according to a conventional method employed in the field of synthetic chemistry of penicillins or cephalosporins. Compound [Ic] is prepared from Compound [Id] without decomposition of its substituents and functional groups in the molecule, employing suitable conditions and reagents. Exemplary conditions for this reaction are described on pages 29-31 of said application Ser. No. 023,645.

When X is an azido group and $R_5$ is converted to H by catalytic reduction, the azido group may be reduced to an amino group. Such a reduced compound having an amino group is also included in the present Compound [Ic].

The present compound is a useful intermediate for producing antibiotics analogous to cephalosporin. For example, cephalosporin analogs having excellent antibacterial activity can be produced by introducing an acyl group employed in the field of the synthetic chemistry of penicillins or cephalosporins, into the amino group of Compound [Ib].

As the salts of the present cephalosporin analogs, inorganic or organic salts such as hydrochlorides, sulfates, carbonates, phosphates, formates, trifluoroacetates and malates of Compound [Ib] represented by the general formula [I] wherein X is an amino group are illustrative. Further, sodium salts, potassium salts, calcium salts, ammonium salts, organic amine salts, and the like of Compound [Ic] represented by the general formula [I] wherein R is a hydrogen atom are also employed.

The acylated compounds of the present invention are represented by the general formula [A-I]:

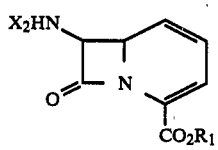
[A-I]

wherein $X_2$ represents an acyl group represented by the general formula $X^1CO$ wherein $X^1$ represents the following five groups:

(1) cyano methyl group or a group represented by the general formula:

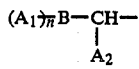

wherein B represents an unsaturated six membered carbocycle, such as cyclohexenyl group, cyclohexadienyl group, phenyl group, etc. or a five or six membered heterocycle such as furyl group, thienyl group, pyrrolyl group, thiazolyl group, oxazolyl group, isothiazolyl group, isoxazolyl group, imidazolyl group, pyrazolyl group, triazolyl group, tetrazolyl group, pyridinyl group, pyrimidinyl group, pyrazinyl group, pyridazinyl group, triazinyl group, 5,6-dihydro-1,4-dithiin-2-yl group, etc.; $A_1$ represents a substituent(s) which is selected from hydrogen atom, hydroxyl group, a lower alkoxy group having 1 to 4 carbon atoms, a halo group, nitro group, amino group, aminomethyl group, methylsulfonamido group, a lower acyloxy group having 1 to 4 carbon atoms; n is a number from 0 to 5; and $A_2$ represents hydrogen atom, amino group, hydroxyl group, carboxyl group or sulfoxyl group;

(2) a group represented by the general formula:

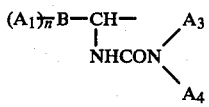

wherein $A_1$, B and n have the same significance as defined above; $A_3$ and $A_4$ are the same or different and represent hydrogen atom, a lower alkyl group having 1 to 4 carbon atoms, a group represented by the general formula:

(wherein $A_5$ means a lower alkyl group having 1 to 4 carbon atoms) or a group represented by the general formula

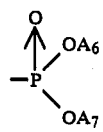

(wherein $A_6$ and $A_7$ are the same or different and represent hydrogen atom, a lower alkyl group having 1 to 4 carbon atoms or an alkali metal); and

also means a group represented by the general formula

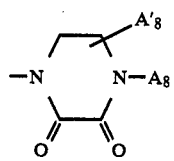

wherein $A_8$ and $A'_8$ are the same or different and include hydrogen atom or a lower alkyl group having 1 to 4 carbon atoms) or a group represented by the general formula

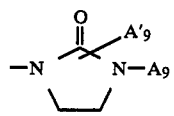

(wherein $A_9$ represents hydrogen atom, a lower alkyl group having 1 to 4 carbon atoms, methylsulfonyl group or furfurylideneimino group, $A'_9$ represents hydrogen atom or a lower alkyl group having 1 to 4 carbon atoms);

(3) a group represented by the general formula:

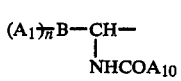

wherein $A_1$, B and n have the same significance as defined above, and $A_{10}$ represents a substituted aryl group or mono-, bi- or tricyclic heterocycles such as a group represented by the following formulae:

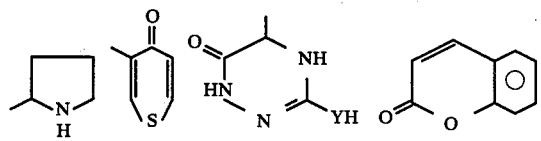

(Y is oxygen or sulfur atom), and a naphthyridinyl group such as

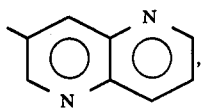

which may have substituents such as those represented by $A_1$ group on rings;

(4) a group represented by the general formula:

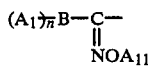

wherein $A_1$, B and n have the same significance as defined above and $A_{11}$ represents hydrogen atom, a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or aryl group, said $A_{11}$ groups being substituted or unsubstituted with suitable substituent(s) such as carboxyl group, cyano group, a halo group, carbamoyl group or lower alkyloxycarbonyl group having 1 to 4 carbon atoms;

(5) a group represented by the general formula

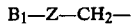

wherein $B_1$ represents trifluoromethyl group, cyanomethyl group, or a group represented by $(A_1)_{\overline{n}}B-$ ($A_1$, n and B have the same significance as defined above) and Z represents oxygen atom or sulfur atom, $R_1$ as set forth in general formula [A-I] represents H or an ester-protecting group conventionally employed in the penicillin and cephalosporin art; that is, an alkyl group having 1 to 5 carbon atoms, such as a methyl group, ethyl group, n-propyl group, iso-propyl group, n-butyl group, isobutyl group, t-butyl group, etc.; a halogenated alkyl group having 1 to 5 carbon atoms, such as chloromethyl group, 2,2,2-trichloroethyl group, 2,2,2-trifluoroethyl group, etc.; an arylmethyl group having 7 to 20 carbon atoms, such as benzyl group, diphenylmethyl group, triphenylmethyl group, etc.; an arylmethyl group having 7 to 20 carbon atoms and having a methoxy group, nitro group, etc., on the phenyl ring; or a substituted silyl group, such as trimethylsilyl group or triphenyl silyl group.

$R_1$ may also be a group enzymatically or non-enzymatically readily eliminable in vivo, for example, a group represented by the general formula

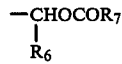

wherein $R_6$ represents hydrogen atom or a lower alkyl group having 1 to 6 carbon atoms, $R_7$ represents a lower alkyl group having 1 to 6 carbon atoms, a lower alkoxy group having 1 to 6 carbon atoms or phenyl group, etc.

In the event that $R_1$ in the general formula [A-I] is hydrogen atom or that $X_2$ is an acyl group having a free carboxyl group or amino group, the compounds represented by the general formula [A-I] may be salts or pharmaceutically acceptable, inorganic or organic bases or acids.

The compounds represented by the general formula [A-I] include all stereoisomers at the 6- and 7-positions and mixtures thereof. Among the stereoisomers, those which have cis-configuration at the 6- and 7-positions have higher antibacterial activities than trans-isomers, so the cis-isomers are more useful as antibiotics.

The =NOR group in the acyl group has the following two geometrical isomers, i.e. syn and anti.

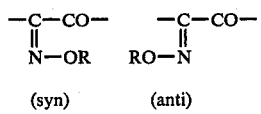

Since the syn-isomer is superior to the anti-isomer in antibacterial activity, the syn-isomer is more useful as an antibiotic. In general, it is known that thiazolyl group represented by

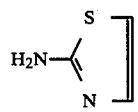

shows reversible interconversion with the thiazolinyl group, as shown below, and both are usually dealt with as identical. In the present specification, both isomers are represented by thiazolyl group.

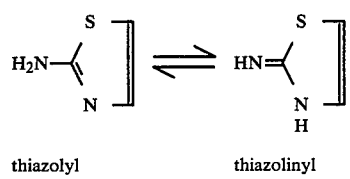

thiazolyl      thiazolinyl

The compounds represented by the general formula [A-I] are produced by acylating the compounds [I-b] according to Flow Sheet IV wherein $R_1$ is R:

Flow Sheet IV

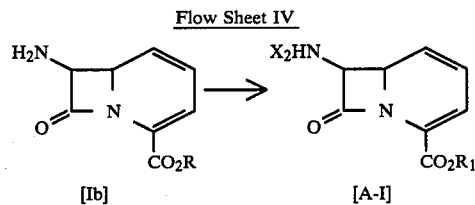

[Ib]      [A-I]

and $X_2$ has the same significance as defined above.

The acylating reaction (condensation) is carried out according to the conventional methods of acylation employed in the field of penicillins and cephalosporins.

The compounds represented by the general formula [A-I] are prepared by (a) the condensation of the compound [Ib] represented by the general formula [Ib], the salt thereof or a compound functionally equivalent thereto (these are referred to as "7-amino compounds" hereinafter) and a carboxylic acid represented by the general formula [III]

$X^2COOH$      [III]

or a reactive derivative thereof and, if necessary, followed by (b) the deprotection of protective group in the group $X^2$- or -$COOR_1$ in a conventional manner.

In the formula [III], $X^2CO-$ corresponds to $X^1CO$; that is $X_2$ in the compound represented by the general formula [A-I]; and $X^2$ represents group $X^1$ defined above or a suitably protected $X^1$ group in the event that $X^1$ has group(s) which are susceptible to acylation, such as hydroxyl group, amino group, carboxyl group or mercapto group.

$X^2$ represents the following five groups, in particular:

(1') cyanomethyl group or a group represented by the general formula:

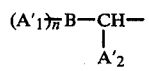

wherein B has the same significance as defined above, $A'_1$ represents a substituent which is selected from the group of hydrogen atom, hydroxy group, a protected hydroxy group, a lower alkoxy group having 1 to 4 carbon atoms, a halo group, nitro group, a protected amino group, a protected aminomethyl group, methylsulfonamido group, a lower acyloxy group having 1 to 4 carbon atoms; n is a number from 0 to 5, and $A'_2$ represents hydrogen atom, a protected amino group, hydroxyl group, a protected hydroxyl group, carboxyl group, a protected carboxyl group, sulfoxyl group or a protected sulfoxyl group;

(2') a group represented by the general formula:

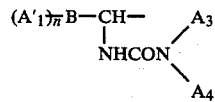

wherein $A'_1$, $A_3$, $A_4$, B and n have the same significance as defined above.

(3') a group represented by the general formula:

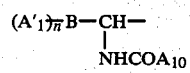

wherein $A'_1$, $A_{10}$, B and n have the same significance as defined above;

(4') a group represented by the general formula:

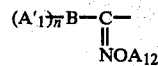

wherein $A'_1$, B and n have the same significance as defined above and $A_{12}$ represents H or a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or an aryl group, those groups being unsubstituted or substituted with suitable substituents, such as a protected carboxyl group, cyano group, a halo group, carbamoyl group or a lower alkyloxycarbonyl group having 1 to 4 carbon atoms;

(5') a group represented by the general formula:

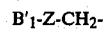

wherein $B'_1$ represents cyano group, trifluoromethyl group, cyanomethyl group, a group represented by $(A'_1)_{\overline{n}}B-$ [wherein $A'_1$, n and B have the same significance as defined above] and Z represents oxygen atom or sulfur atom.

As the protecting group(s) for amino group, hydroxyl group or carboxyl group in the $X^2$ group, those which are typically employed in cephalosporin or penicillin chemistry are used.

As the compound functionally equivalent to Compound [Ib], 7-monosilyl or 7-disilyl amino derivatives of Compound [Ib] are illustrative.

Exemplary of the reactive derivatives of the carboxylic acid represented by the general formula [III], $X^2COOH$ are: (1) an acid halide, (2) an acid anhydride, (3) a mixed acid anhydride, (4) an active ester, (5) an active thioester, and (6) an acid azide, and the like.

Condensation (acylation) reactions using the above derivatives are illustrated as follows.

(1) Method using an Acid Halide

A 7-amino compound and an acid halide are subjected to a condensation reaction in an inactive solvent and, additionally preferably in the presence of a proton acceptor.

The acid halide is prepared in a conventional manner.

The proton acceptor is, for example, an inorganic or organic base and, preferably, sodium carbonate, potassium carbonate, sodium hydroxide, potassium hydroxide, triethylamine, N-methylmorphine, pyridine, and the like.

The solvent is any inactive solvent which does not affect the reaction. Preferably, the solvent is water, an ether; such as tetrahydrofuran, dimethoxyethane, and the like; an ester such as ethyl acetate; an amide such as dimethylacetamide, hexamethylphosphoric triamide, or a sulfoxide, such as dimethylsulfoxide, or mixtures thereof.

The reaction is carried out at a temperature of $-20°$ to $40°$ C., preferably from $0°$ C. to room temperature.

(2) Method using an Acid Anhydride

A 7-amino compound and an acid anhydride are subjected to a condensation reaction in an inactive solvent.

The acid anhydride is prepared in a conventional manner.

The solvent is any solvent which does not affect the reaction. Preferably, the same solvents as those in the above Method (1) are employed. The range of reaction temperatures is the same as used in the above Method (1).

A typical acid anhydride method uses a carbodiimide, such as dicyclohexylcarbodiimide.

(3) Method using a Mixed Acid Anhydride

A 7-amino compound and a mixed acid anhydride are subjected to a condensation reaction in an inactive solvent.

The mixed acid anhydride is prepared in a conventional manner. For example, a corresponding carboxylic acid, $X^2COOH$, and a chloroformic ester, such as ethyl chloroformate or isobutyl chloroformate are reacted in the presence of a base.

As the solvent, any inactive solvent which does not affect the reaction is employed. Generally, an anhydrous solvent or a mixture of water and an anhydrous solvent and preferably the same solvent as in the above Methods (1) and (2) is utilized.

The range of reaction temperatures is the same as in the above Methods.

(4) Method using an Active Ester

A 7-amino compound and an active ester are subjected to a condensation reaction in an inactive solvent.

The solvent and reaction temperatures are the same as those used in the above Methods 1-3.

As the active ester, a phenylester, such as p-nitrophenyl ester, trichlorophenyl ester; a methyl ester having an electronegative group, such as cyanomethylester, and N-hydroxydiacylimide ester, such as N-hydroxysuccinimide ester are employed.

The active ester may be prepared in accordance with conventional techniques. For example, a corresponding carboxylic acid and an hydroxyl compound are reacted in the presence of a dehydrating condensation reagent, such as dicyclohexylcarbodiimide to form the active ester.

(5) Method using an Active Thiolester

This method is carried out in a similar manner as described in Method (4).

The most preferable thiolester is p-nitrothiophenyl ester. It is prepared by the mixed acid anhydride method or dicyclohexylcarbodiimide method described hereinabove.

(6) Method using an Acid Azide

A 7-amino compound and an acid azide compound are subjected to a condensation reaction in an inactive solvent in a similar manner as that set forth in the above Methods 1-5.

The acid azide is prepared by reacting the hydrazide of a corresponding carboxylic acid with nitrous acid at a temperature of $-20°$ to $0°$ C.

In the event that reactive derivatives of the carboxylic acid mentioned above have an amino group, hydroxyl group, carboxyl group or mercapto group susceptible to acylation, then those groups are preferably protected with a suitable protecting group prior to the condensation reaction with the amino compounds.

A suitable protecting group includes those used in the field of penicillin and cephalosporin synthetic chemistry.

The amino-protecting group is preferably a t-butyloxycarbonyl group (Boc), benzyloxycarbonyl group (Cbz), trichloroethyloxycarbonyl group, trityl group, formyl group, chloroacetyl group, trialkylsilyl group, proton, β-diketone, β-ketoester, and the like.

As a compound protected with a proton, the compound represented by the formula:

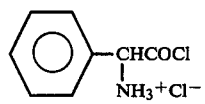

is typical.

As a compound protected with a β-ketoester, the compound represented by the formula:

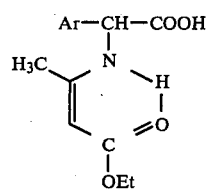

is illustrative.

The hydroxyl-protecting group is usually a benzyl group, benzyloxycarbonyl group, trityl group, tetrahydropyranyl group, t-butyl group and the like. Since the reactivity (nucleophilic activity) of most amino groups is higher than that of the hydroxyl group, protection of the hydroxyl group may not be essential, depending on the acylation method employed.

The carboxyl-protecting group is usually a t-butyl group, benzyl group, p-methoxybenzyl group, p-nitrobenzyl group, benzhydryl group, or the like.

The mercapto-protecting group may be a benzyl group, trityl group, benzyloxycarbonyl group, p-nitrobenzyl group, or the like.

Deprotection of the above protecting groups is carried out in the conventional manner commonly used in the field of the synthetic chemistry of penicillins and cephalosporins.

Various methods of deprotecting amino-protecting groups are utilized. Among them the following conventional techniques are exemplified:

The Boc group is deprotected by the method using an acid, such as formic acid, acetic acid, trifluoroacetic acid, hydrochloric acid, and the like.

The Cbz group is deprotected by catalytic reduction or a method using hydrogen bromide-acetic acid, or the like.

The trityl group is deprotected by a catalytic reduction or a method using an acid, such as trifluoroacetic acid, or the like.

The formyl group is deprotected by hydrolysis using an acid or an alkali.

The chloroacetyl group is deprotected by a method using thiourea.

The trialkylsilyl group is deprotected by hydrolysis.

A proton is deprotected by neutralization.

The additive with β-diketone or β-ketoester is removed by acid hydrolysis.

To deprotect hydroxyl-protecting groups, the following methods can be employed:

Benzyl group is deprotected by a catalytic reduction or a method using hydrogen fluoride.

Cbz group is deprotected by a catalytic reduction or a method using hydrogen bromide-acetic acid.

Trityl group is deprotected by a catalytic reduction or a method using trifluoroacetic acid or the like.

Tetrahydropyranyl group is deprotected by acid hydrolysis.

t-Butyl group is deprotected by a method using an acid such as trifluoroacetic acid, hydrogen bromide-acetic acid, hydrogen chloride or the like.

To protect carboxyl-protecting groups, the following techniques are exemplary.

t-Butyl group is deprotected by a method using an acid such as trifluoroacetic acid.

Benzyl or p-nitrobenzyl group is deprotected by a catalytic reduction or a method using a Lewis acid, such as $AlCl_3$, or the like.

Benzhydryl or p-methoxybenzyl group is deprotected by a catalytic reduction or a method using hydrogen bromide-acetic acid, hydrogen chloride-methanol, trifluoroacetic acid, or the like.

As a method for deprotecting mercapto-protecting groups, the following are exemplified:

Benzyl group is deprotected by a method using hydrogen fluoride or the like; Cbz group is deprotected by a method using hydrogen bromide-acetic acid, trifluoroacetic acid, or the like.

p-Nitrobenzyl group is deprotected by a catalytic reduction. The deprotection mentioned above may well be carried out concomitantly with the conversion of R group to hydrogen atom; that is, deesterification.

If desired, the acylating reaction is preferably promoted by silylating the starting compound [Ib] with a silylating agent, such as trimethylchlorosilane-base, hexamethyldisilazane, N,O-bistrimethylsilylacetamide, or the like to solubilize the starting material in an organic solvent and to activate the amino group.

The present compounds represented by the general formula [A-I] wherein $R_1$ is H, provide excellent antibacterial activity against Gram-positive and Gram-negative bacteria and they are expected to be useful as antiinfectional agents or antibacterial agents against these bacteria. The compounds represented by the general formula [A-I], wherein $R_1$ is other than H, also can be used as the starting material of the compounds represented by the general formula [A-I] wherein $R_1$ is H.

The invention includes within its scope pharmaceutical compositions comprising, as an active ingredient, Compound [A-I] or a pharmaceutically acceptable salt thereof in association with a pharmaceutical carrier or diluent. The compounds of this invention are administered by parenteral (intramuscular, intraperitoneal, intravenous, or subcutaneous injection routes), oral or rectal routes of administration and can be formulated in dosage forms appropriate for each route of administration.

Preparations according to this invention for parenteral administration include sterile aqueous or nonaqueous solutions, suspensions, or emulsions. Examples of nonaqueous solvents or vehicles for such solutions, suspensions or emulsions are propylene glycol, polyethylene glycol, vegetable oils, such as olive oil, and injectable organic esters, such as ethyl oleate. Such dosage forms may also contain adjuvants such as preserving, wetting, emulsifying, and dispersing agents. Preparations may be sterilized by filtration through a bacteria-retaining filter, by incorporation of sterilizing agents into the compositions, by irradiation of the compositions, or by heating the compositions. Dosage forms can also be manufactured in the form of sterile solid compositions which can be dissolved in sterile water, or some other sterile injectable medium immediately before use.

Compositions for oral administration may be presented in a form suitable for absorption by the gastrointestinal tract. Tablets and capsules for oral administration may be in unit dose presentation form. They may contain conventional excipients such as binding agents, for example, gelatin, syrup, acacia, sorbitol, tragacanth, or polyvinylpyrrolidone; fillers, such as lactose, sugar, maize-starch, calcium, phosphate, sorbitol or glycine; lubricants, for example, magnesium stearate, talc, polyethylene glycol, silica; disintegrants such as potato starch or acceptable wetting agents, such as sodium lauryl sulphate. The tablets may be coated according to methods well known in the art. Oral liquid preparations may be in the form of aqueous or oily suspensions, solutions, emulsions, syrups, or the like. Alternatively, preparations may be provided as a dry product for reconstitution with water or other suitable vehicles before use. Such liquid preparations may contain conventional additives such as suspending agents, including sorbitol syrup, methyl cellulose, glucose sugar-syrup, gelatin, hydroxyethylcellulose, carboxymethylcellulose, aluminum stearate gel; emulsifying agents, for example, lecithin or sorbitan monooleate; nonaqueous vehicles, including edible oils (such as almond oil or coconut oil), propylene glycol, or ethyl alcohol; preservatives, for example, methyl or propyl p-hydroxybenzoates or sorbic acid.

Compositions for rectal administration are preferably suppositories which may contain, in addition to the active substance, excipients such as cocoa butter or a suppository wax.

The dosage of active ingredients, in the compositions of this invention may be varied; however, sufficient amounts of the active ingredient(s) are employed to obtain a suitable dosage form. The selected dosage depends upon the desired therapeutic effect, on the route of administration, and on the duration of the treatment. Generally, dosage levels of between about 5 to 350 mg/kg. of body weight daily are administered to mammalian patients to achieve an antibiotic effect.

As the pharmaceutically acceptable salt of Compound [A-I], inorganic salts and organic salts such as hydrochloride, sulfate, carbonate, phosphate, formate, malate, etc. are mentioned. Further, the sodium salt, potassium salt, calcium salt, ammonium salt, organic amine salt, etc. of the carboxylic acid represented by the general formula [A-I] wherein $R_1$ is hydrogen are exemplified. The salts are prepared in a conventional method.

The following Examples show practical embodiments for preparing preferred species of the present compounds and are not limitative of scope.

EXAMPLE 1

Preparation of t-butyl (±)-cis-7-azido-1-azabicyclo[4,2,0]oct-2,4-diene-8-on-2-carboxylate (the cis compound represented by the general formula [I] wherein X is $N_3$ and R is $^tBu$ and represented by the following formula).

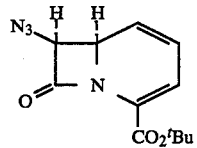

Hereinafter, cis relates to the configuration of protons at the 6- and 7-positions.

(1) In this Example, 960 mg (2.47 mmole) of t-butyl (±)-cis-5-phenylsulfinyl-7-azido-1-azabicyclo[4,2,0]oct-2-en-8-on-2-carboxylate A (the sulfinyl group at the 5-position has the same configuration as protons at the 6- and 7-positions and which is a new compound prepared in Example 11 mentioned below) is dissolved in 50 ml of toluene and the solution is stirred at a temperature of 105° to 110° C. for 3.5 hours. The solvent is removed by distillation under reduced pressure to obtain a crude product. The product is charged on a column packed with 50 g of silica gel [Wako-gel C-200, product of Wako Junyaku Co. Ltd. The same silica gel is used hereinafter] and elution is carried out with a mixture of n-hexane and ethyl acetate [8:1 (by volume, the same shall apply hereinafter)]. The eluate is concentrated under reduced pressure to obtain 330 mg of a colorless, transparent oily product. Yield 50.9%. Properties of the product are as follows.

NMR δ(CDCl$_3$): 6.64 (d, 1H, J=6 Hz), 6.24 (ddd, 1H, J=2.5, 6.0, 6.0 Hz), 6.04 (dd, 1H, J=2.0, 10.0 Hz), 5.26 (d, 1H, 5.0 Hz), 4.64 (m, 1H), 1.50 (s, 9H)

IR $\nu_{max}^{CHCl_3}$(cm$^{-1}$): 2130, 1790, 1720, 1630

(2) In this Example, 895 mg (2.30 mmole) of t-butyl (±)-cis-5-phenylsulfinyl-7-azido-1-azabicyclo[4,2,0]oct-2-en-8-on-2-carboxylate B (the phenylsulfinyl group at the 5-position, which has the reverse configuration to protons at the 6- and 7-positions and which is a new compound prepared according to a similar method described in Example 11) is dissolved in 50 ml of carbon tetrachloride and the solution is stirred at a temperature of 80° C. for 1.5 hours. The solvent is removed by distillation under reduced pressure to obtain a crude product. The product is subjected to purification as in Example 1—1) to obtain 449 mg of the desired compound. Yield 74.3%. Properties of the compound agree with those obtained in Example 1—1).

EXAMPLE 2

Preparation of (±)-cis-7-azido-1-azabicyclo[4,2,0]oct-2,4-diene-8-on-2-carboxylic acid {the cis compound represented by the general formula [I] wherein X is N$_3$ and R is H and represented by the following formula}.

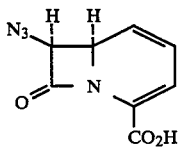

In this Example, 290 mg (1.1 mmole) of t-butyl (±)-cis-7-azido-1-azabicyclo[4,2,0]oct-2,4-diene-8-on-2-carboxylate obtained as in Example 1 is dissolved in a mixture of 6 ml of trifluoroacetic acid and 6 ml of methylene chloride and the solution is stirred under ice cooling for 1 hour and 40 minutes and further at room temperature for 30 minutes. The solvent is removed by distillation under reduced pressure. After adding ethyl acetate, the residue is extracted 3 times with 5 ml of 10% potassium carbonate. About 15 ml of extracted aqueous solution is adjusted to pH 2.5 with 1 N-hydrochloric acid and extracted 2 times with 10 ml of ethyl acetate. The extracts are dried with sodium sulfate and the solvent is removed by distillation under reduced pressure to obtain 156 mg of the desired compound as crystals. Yield 68.4%. Properties of the compound are as follows.

NMR δ(CD$_3$OD): 6.77 (d, 1H, J=6.0 Hz), 6.33 (m, 1H), 6.13 (dd, 1H, J=2.0, 10.0 Hz), 5.48 (d, 1H, J=5.0 Hz)

IR $\nu_{max}^{KBr}$ (cm$^{-1}$): 2130, 1780, 1700, 1620

Melting point: 125°–126° C.

Mass: M+ (m/e) 206

EXAMPLE 3

Preparation of (±)-cis-7-amino-1-azabicyclo[4,2,0]oct-2,4-diene-8-on-2-carboxylic acid {the cis compound represented by the general formula [I] wherein X is NH$_2$ and R is H and represented by the following formula}.

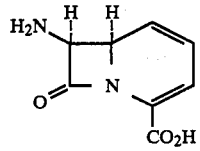

In this Example, 39 mg (0.19 mmole) of (±)-cis-7-azido-1-azabicyclo[4,2,0]oct-2,4-diene-8-on-2-carboxylic acid obtained as in Example 2 is dissolved in 3 ml of ethanol and 22 mg of 5% palladium-calcium carbonate (catalyst) is added. The mixture is stirred at atmospheric pressure in a stream of hydrogen gas for 5 hours and 45 minutes. The catalyst is removed by filtration and washed with 3 ml of ethanol and 3 ml of water. The filtrate and washings are combined and concentrated under reduced pressure. After adding 3 ml of ethyl acetate, the concentrate is extracted with 5 ml of water. The water layer is concentrated to dryness under reduced pressure to obtain 35.4 mg of the desired compound. Yield 100%. Properties of the compound are as follows.

IR $\nu_{max}^{KBr}$ (cm$^{-1}$): 3430, 1785, 1645, 1615

Rf value on silica gel thin layer chromatography using a mixture of n-butanol, acetic acid and water (4:1:1) and Kieselgel 60 #5719 (product of E. Merck & Co.): 0.09

EXAMPLE 4

Preparation of t-butyl (±)-cis-7-amino-1-azabicyclo[4,2,0]oct-2,4-diene-8-on-2-carboxylate represented by the following formula:

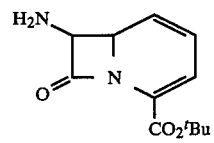

In this Example, 250 mg of t-butyl (±)-cis-7-azido-1-azabicyclo[4,2,0]oct-2,4-diene-8-on-2-carboxylate obtained as in Example 1 is dissolved in 30 ml of methylene chloride and 0.4 ml of triethylamine is added. Hydrogen sulfide is bubbled into the mixture for about 3 minutes. After stirring at room temperature for 2.5 hours, nitrogen is bubbled into the mixture for 30 minutes and the solvent is distilled off. To the residue, ethyl acetate is added and the mixture is extracted with 10% aqueous citric acid. The extract is adjusted to pH about 7 with potassium carbonate and extracted with ethyl acetate. The extract is dried and the solvent is distilled off to obtain 168 mg (74.6%) of the desired compound. Properties of the compound are set forth below.

IR $\nu_{max}^{KBr}$ (cm$^{-1}$): 1770, 1710, 1630

NMR δ(CDCl$_3$): 6.60 (d, 1H, J=6 Hz), 6.30 (ddd, 1H, J=10, 6, 2.5 Hz), 6.05 (dd, 1H, J=10, 2 Hz), 4.88 (d, 1H, J=5 Hz), 4.58 (m, 1H), 1.58 (s, 9H)

EXAMPLE 5

Preparation of the trifluoroacetate of (±)-cis-7-amino-1-azabicyclo[4,2,0]oct-2,4-diene-8-on-2-carboxylic acid represented by the following formula:

17

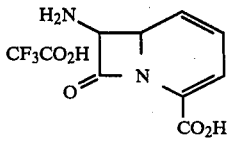

In this Example, 120 mg of t-butyl (±)-cis-7-amino-1-azabicyclo[4,2,0]oct-2,4-diene-8-on-2-carboxylate obtained in Example 4 is dissolved in 0.5 ml of 30% trifluoroacetic acid solution in methylene chloride and 40 μl of anisole is added. The mixture is stirred at room temperature for 1.5 hours and the solvent is distilled off. Ether is added to the resulting residue and the desired compound is obtained by filtration as a powder. Properties of the product are set forth below.

IR $\nu_{max}^{KBr}$ (cm$^{-1}$): 1800, 1785, 1675, 1620

NMR δ(D$_2$O): 6.62 (d, 1H, J=5.8 Hz), 6.42 (ddd, 1H, J=2.4, 5.8, 9.5 Hz), 6.12 (dd, 1H, J=1.2, 9.7 Hz), 5.22 (d, 1H, J=4.6 Hz), 4.91 (m, 1H)

EXAMPLE 6

Preparation of (±)-cis-7-[2-(2-amino-4-thiazolyl)-2-anti-methoxyiminoacetamido]-1-azabicyclo[4,2,0]oct-2,4-diene-8-on-2-carboxylic acid represented by the following formula:

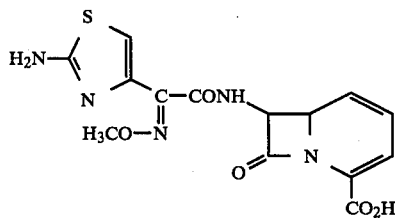

In this Example, 66 mg of 2-(N-trityl-2-amino-4-thiazolyl)-2-anti-methoxyimino acetic acid is dissolved in 1 ml of tetrahydrofuran and 150 μl of 1 N N-methylmorpholine solution in tetrahydrofuran is added. Further, 150 μl 1 N isobutyl chloroformate solution in tetrahydrofuran is added under ice cooling and the mixture is stirred under ice cooling for about 25 minutes. Then, 40 mg of a solution of the trifluoroacetate of (±)-cis-7-amino-1-azabicyclo[4,2,0]oct-2,4-diene-8-on-2-carboxylic acid obtained as in Example 5 in 21 μl of triethylamine and 500 μl of bis-silyl acetamide is added dropwise to the mixture. The resulting mixture is stirred under ice cooling for 2 hours and at room temperature for one hour. After adding ethyl acetate, the reaction mixture is washed with 1 N hydrochloric acid and saturated sodium chloride solution, dried and solvent is evaporated to obtain 108 mg of a crude product. Properties of the product are as follows.

IR $\nu_{max}^{KBr}$ (cm$^{-1}$): 1770, 1670

The crude product obtained above (99 mg) is dissolved in 2 ml of 50% aqueous acetic acid and the solution is stirred at a temperature of 50° to 55° C. for about 15 minutes. After adding ethyl acetate, the reaction mixture is extracted with water. The aqueous layer is concentrated under reduced pressure and the concentrate is subjected to chromatography using about 30 ml of HP-10. Elution is carried out with a mixture of water and methanol (5:1-3:1-1:1). Eluates are combined and concentrated under reduced pressure to obtain 1.8 mg

18 of the desired compound. Yield 3.6%. Properties of the compound are set forth below.

IR $\nu_{max}^{KBr}$ (cm$^{-1}$): 1770, 1670–1680, 1630, 1530–1540

NMR δ(CD$_3$OD): 7.55 (s, 1H), 6.71 (d, 1H, J=4.5 Hz), 6.31 (dd, 1H, J=1.7, 10.3 Hz), 6.18 (d, 1H, J=10.3 Hz), 5.84 (d, 1H, J=4.6 Hz), 4.08 (s, 3H)

EXAMPLE 7

Preparation of (±)-cis-7-[2-N-chloroacetyl-2-amino-4-thiazolyl)-2-syn-methoxyiminoacetamido]-1-azabicyclo[4,2,0]oct-2,4-diene-8-on-2-carboxylic acid represented by the following formula:

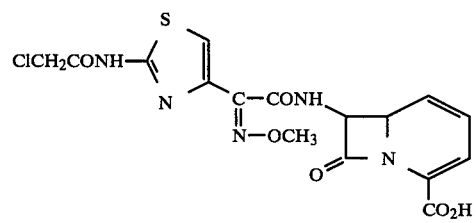

In this example, 75 mg of 2-(N-chloroacetyl-2-amino-4-thiazolyl)-2-syn-methoxyiminoacetic acid is dissolved in 1.4 ml of dichloromethane and 45 μl of triethylamine is added. To the solution 56 mg of phosphorous pentachloride is added and the mixture is stirred at room temperature for 30 minutes. After adding 5 ml of n-hexane, the mixture is stirred and the supernatant is removed by decantation. To the residue 2.7 ml of tetrahydrofuran is added. The mixture is added to a solution of 60 mg of the trifluoroacetate of (±)-cis-7-amino-1-azabicyclo[4,2,0]oct-2,4-diene-8-on-2-carboxylic acid in 3 ml of 50% aqueous tetrahydrofuran and 120 μl of triethylamine under ice cooling. The mixture is stirred for about 2.5 hours and acidified to a pH of 2 to 3 with 1 N hydrochloric acid. The solution is extracted with ethyl acetate. The extract is washed with saturated sodium chloride solution, dried and concentrated under reduced pressure. The residue is triturated with ether and 35 mg (39.0%) of the desired product is obtained by filtration as a powder. Properties of the product are as follows:

IR $\nu_{max}^{KBr}$ (cm$^{-1}$): 1765, 1700–1710, 1690, 1660, 1550

NMR δ(CD$_3$OD): 7.50(s, 1H), 6.8(m, 1H), 6.1–6.4(m, 2H), 5.9(m, 1H), 4.3(s, 2H), 4.0(s, 3H)

EXAMPLE 8

Preparation of (±)-cis-7-[2-(2-amino-4-thiazolyl)-2-syn-methoxyiminoacetamido]-1-azabicyclo[4,2,0]oct-2,4-diene-8-on-2-carboxylic acid represented by the following formula:

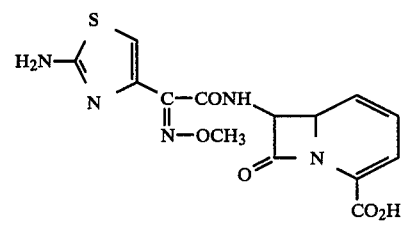

In this Example, 15 mg of (±)-cis-7-[2-(N-chloroacetyl-2-amino-4-thiazolyl)-2-syn-methoxyiminoacetamido]-1-azabicyclo[4,2,0]oct-2,4-diene- 8-on-2-carboxylic acid obtained in Example 7 is dissolved in 0.3 ml of dimethyl acetamide and 5.3 mg of thiourea is added. The mixture is stirred at room temperature for about 18 hours. Ether is added to the mixture and the supernatant is removed by decantation. The residue is subjected to chromatography using about 6 ml of HP-20.

Elution is carried out with a mixture of water and methanol (4:1-3:1-2:1-1:1). Eluates are combined and concentrated under reduced pressure to obtain 10.2 mg (77.2%) of the desired compound. Properties of the compound are set forth below.

IR $\nu_{max}^{KBr}$ (cm$^{-1}$): 1770, 1650-1670, 1630, 1540

NMR $\delta$(D$_2$O): 7.05(s, 1H), 6.64(d,1H, J=5.4 Hz), 6.25 (m, 1H), 6.06(d, 1H), 5.85(d, 1H, J=4.6 Hz), 4.01(s, 3H)

EXAMPLE 9

Antibacterial activities of the compounds obtained in Examples 6 and 8 are measured according to the Heart Infusion Agar Dilution Method (pH 7.2). The results are set forth below. Cefazolin is used as a control.

| Microorganism | MIC ($\gamma$/ml) | | |
|---|---|---|---|
| | The compound obtained in Example 6 | The compound obtained in Example 8 | Cefazolin |
| Staphylococcus aureus 209-P | ≧50 | ≧50 | <0.05 |
| Staphylococcus aureus Smith | ≧50 | ≧50 | 0.4 |
| Staphylococcus epidermidis | ≧50 | ≧50 | 0.78 |
| Escherichia coli NIHJC-2 | ≧50 | 25 | 1.56 |
| Escherichia coli GN 2411-5 | ≧50 | 25 | — |
| Escherichia coli Juhl | ≧50 | 50 | 1.56 |
| Klebsiella pneumoniae 8045 | 50 | 6.25 | 0.78 |
| Klebsiella pneumoniae Y-60 | ≧50 | ≧50 | 3.12 |
| Serratia marcescens T-26 | ≧50 | ≧50 | >100 |
| Serratia marcescens T-55 | ≧50 | 50 | 50 |
| Proteus mirabilis 1287 | ≧50 | 6.25 | 12.5 |
| Proteus vulgaris 6897 | ≧50 | 6.25 | 12.5 |
| Proteus morganii KY4298 | ≧50 | 12.5 | >100 |
| Proteus rettgeri KY4289 | ≧50 | 6.25 | 25 |
| Pseudomonas aeruginosa No. 1 | ≧50 | ≧50 | — |
| Pseudomonas aeruginosa 145 | ≧50 | ≧50 | >100 |
| Pseudomonas putida F264 | ≧50 | 12.5 | >100 |

EXAMPLE 10

Preparation of ($\pm$)-cis-7-[2-(thiophene-2-yl)acetylamino]-1-azabicyclo[4,2,0]oct-2,4-diene-8-on-2-carboxylic acid (the compound represented by the following formula ):

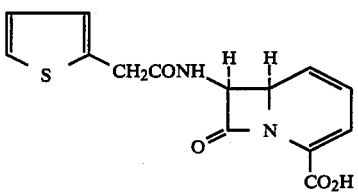

In this Example, 50 mg of ($\pm$)-cis-7-amino-1-azabicyclo[4,2,0]oct-2,4-diene-8-on-2-carboxylic acid obtained in Example 3 is dissolved in 2.4 ml of water and 2.4 ml of acetone, and 76 mg of sodium bicarbonate is added. To the mixture, 44 mg of thienylacetylchloride dissolved in 0.2 ml of acetone is added under ice cooling. After an insoluble product is formed in 5 minutes, 2 ml of acetone is further added to make the mixture homogeneous and the resulting mixture is stirred under ice cooling for 1 hour and 50 minutes. The reaction mixture is adjusted to pH 2.0 with 3 ml of 1 N hydrochloric acid and the solvent is removed by distillation under reduced pressure to obtain 60 mg of a crude product. The product is triturated with 1 ml of ether and filtered to obtain 23 mg of the desired product. Yield 27.2%. Properties of the product are as follows.

IR $\nu_{max}^{KBr}$ (cm$^{-1}$): 1790, 1780, 1695, 1655, 1630

NMR $\delta$(CD$_3$OD): 7.2-7.3(m, 1H), 6.93-6.97(m, 2H), 6.72(d, 1H, J=5.8 Hz), 6.21(ddd, 1H, J=2.2, 5.8, 9.8 Hz), 5.89(dd, 1H, J=1.5, 9.8 Hz), 5.72(d, 1H, 4.6 Hz), 4.67-4.73(m, 1H), 3.80(s, 2H)

Antibacterial activities of the product obtained in this Example are measured according to the Heart Infusion Agar Dilution Method (pH 7.0). The results are set forth below.

| Microorganism | MIC ($\gamma$/ml) |
|---|---|
| Vibrio percolans KY4174 | 55.6 |
| Erwinia aroides KY3241 | 13.9 |
| Staphylococcus aureus KY4279 | 27.8 |
| Escherichia coli KY4271 | >55.6 |
| Bacillus subtilis KY4273 | 55.6 |
| Proteus vulgaris KY4277 | 27.8 |
| Shigella sonnei KY4281 | >55.6 |
| Salmonella typhosa KY4278 | 13.9 |
| Klebsiella pneumonia KY4275 | 27.8 |

EXAMPLE 11

Preparation of t-butyl ($\pm$)-cis-5-phenylsulfinyl-7-azido-1-azabicyclo[4,2,0]oct-2-en-8-on-2-carboxylate A [the starting compound used in Example 1—1)] and t-butyl ($\pm$)-cis-5-phenylsulfinyl-7-azido-1-azabicyclo[4,2,0]oct-2-en-8-on-2-carboxylate B [the starting compound used in Example 1-2)]

(1) Preparation of the Schiff's base represented by the formula:

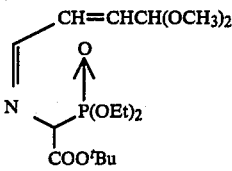

In this Example, 1.08 g (4 mmoles) of t-butyl-$\alpha$-amino-diethylphosphonoacetate is dissolved in 100 ml of anhydrous methylene chloride and 580 mg (4.4 mmoles of 4,4-dimethyl-trans-2-butenal dissolved in 20 ml of anhydrous methylene chloride is added thereto. The mixture is stirred at room temperature for one hour. Anhydrous magnesium sulfate (600 mg) is added to the mixture and the resulting solution is stirred additionally for one hour. The reaction solution is subjected to filtration under reduced pressure and the methylene chloride is evaporated under reduced pressure to obtain 1.63 g of an oily product. Yield 100%.

The product is identified as the desired Schiff's base from the properties described below.

NMR $\delta$(CDCl$_3$)ppm: 8.00(1H, dd), 6.67(1H, dd), 4.93(1H, d), 3.97-4.33(4H, m), 3.33 (6H, s), 1.50(9H, s), 1.33(6H, t)

Mass (m/e): 380 (M$^+$+1)

(2) Preparation of the acetal compound represented by the formula:

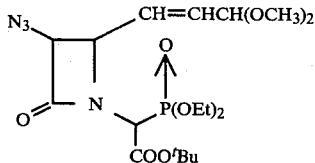

and the aldehyde compound represented by the formula:

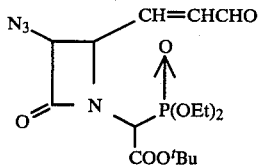

In this Example, 1.6 g (4.2 mmole) of the Schiff's base obtained as in Example 11-1) is dissolved in 30 ml of anhydrous benzene and 30 ml of anhydrous cyclohexane and 0.84 ml (7 mmoles) of anhydrous triethylamine is added. To the mixture, 580 mg (4.8 mmoles) of azidoacetylchloride dissolved in 40 ml of cyclohexane is added dropwise and slowly at room temperature in about 1.5 hours. The mixture is further stirred at room temperature for one hour. Benzene is added to the reaction solution and the mixture is washed with saturated sodium bicarbonate and saturated sodium chloride solution. The resulting solution is dried with anhydrous magnesium sulfate and concentrated under reduced pressure to obtain 1.88 g of a crude product. The product is charged on a column packed with 90 g of silica gel and elution is carried out with a solvent of n-hexane and ethyl acetate (1:2). The acetal compound [550 mg (28.2%)] and 220 mg (11.3%) of the aldehyde compound are obtained. Properties of the obtained acetal and aldehyde compounds are as follows. The acetal compound NMR δ(CDCl$_3$)ppm: 5.83–6.07(2H, m), 4.50–5.00(3H, m), 4.23(4H, q), 3.33(6H, s), 1.50(9H, s), 1.37(6H, t)

IR $\nu_{max}^{CHCl_3}$ (cm$^{-1}$): 2120, 1780, 1745

The aldehyde compound

IR $\nu_{max}^{CHCl_3}$ (cm$^{-1}$): 2120, 1785, 1750, 1700

NMR δ(CDCl$_3$)ppm: 9.62(1H, d), 7.00(1H, dd, J=8, 15 Hz), 6.26(1H, dd, J=7, 15 Hz), 4.84(1H, d, J=24 Hz), 4.80–5.02(2H, m), 4.16(4H, m), 1.46(9H, s), 1.26(6H, dt)

Mass (m/e) 417 (M$^+$+1)

(3) Preparation of the thiophenyl compound represented by the formula:

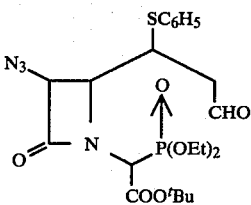

Fifty percent sodium hydride [120 mg (2.5 mmoles)] is added to a mixture of 970 mg (8.8 mmoles) of thiophenol and 6.5 ml of absolute ethanol. After the reaction of sodium hydride is completed, the reaction solution is cooled to a temperature of −78° C. on dry ice-methanol bath, and 920 mg (2.2 mmoles) of the aldehyde compound which is obtained as in the above and dissolved in 6.5 ml of ethanol is added dropwise thereto in about 15 minutes. The mixture is stirred at a temperature of from −78° to −20° C. for 2 hours. Acetic acid and water are added to the mixture to raise the temperature to room temperature. The solution is subjected to ether extraction and the ether layer is washed with saturated sodium chloride solution. The washing is dried with anhydrous sodium sulfate and concentrated under reduced pressure to obtain 1.12 g of an oily product. The product is charged on a column packed with 60 g of silica gel and elution is carried out with a solvent of n-hexane and ethyl acetate (2:1). 470 mg (40.4%) of the thiophenyl compound is obtained. Properties of the product are described below.

IR $\nu_{max}^{CHCl_3}$ (cm$^{-1}$): 2120, 1780, 1735

Mass (m/e): 526 (M$^+$)

(4) Preparation of t-butyl (±)-cis-5-phenylthio-7-azido-1-azabicyclo[4,2,0]oct-2-en-8-on-2-carboxylate represented by the following formula:

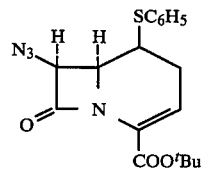

The thiophenyl compound obtained as in Example 11-3) [470 mg (0.89 mmole)] is dissolved in 14 ml of anhydrous dimethoxyethane and 47 mg (0.98 mmole) of 50% sodium hydride is added thereto. The mixture is stirred at room temperature for 3.5 hours and ether is added thereto. The mixture is washed with saturated aqueous ammonium chloride and saturated sodium chloride solution and dried with anhydrous sodium sulfate. The resulting solution is concentrated under reduced pressure to obtain 340 mg of an oily product which is a mixture of stereoisomers at the 5-position of the desired compound.

The oily product is charged on a column packed with 15 g of silica gel and elution is carried out with a solvent of n-hexane and ethyl acetate (4:1, by volume) to obtain two types of isomers. These isomers have the following properties and are identified as the less polar isomer (configuration of SC$_6$H$_5$ is the same as those of protons at the 6- and 7-positions) of the desired compound and the more polar isomer (configuration of SC$_6$H$_5$ is reverse to those of protons at the 6- and 7-positions). The less polar isomer A': Yield 80 mg (9.7%)

IR $\nu_{max}^{CHCl_3}$ (cm$^{-1}$): 2130, 1790, 1725, 1640

NMR δ(CDCl$_3$)ppm: 7.24–7.56 (5H, m), 6.21(1H, dd, J=3.0, 5.5 Hz), 5.06(1H, d, J=5 Hz), 3.65(1H, dd, J=5, 11 Hz), 3.19(1H, ddd, J=5.5, 11, 11 Hz), 2.74(1H, ddd, J=5.5, 5.5, 19 Hz), 2.29(1H, ddd, J=3, 11, 19 Hz), 1.50(s, 9H)

Mass (m/e): 372 (M$^+$)

The more polar isomer B': Yield 125 mg (15.2%)

IR $\nu_{max}^{CHCl_3}$ (cm$^{-1}$): 2120, 1790, 1720, 1630

Mass (m/e): 372 (M$^+$)

NMR δ(CDCl$_3$)ppm: 7.20–7.52(5H, m), 6.12(1H, dd, J=3.5, 4.5 Hz), 4.98(1H, d, J=5 Hz), 3.99(1H, dd, J=2.5, 5.0 Hz), 3.82(1H, m), 2.58–2.70(2H, m), 1.54(9H, s)

(5) Preparation of t-butyl (±)-cis-5-phenylsulfinyl-7-azido-1-azabicyclo[4,2,0]oct-2-en-8-on-2-carboxylate A In this Example, 110 mg (0.296 mmole) of t-butyl (±)-cis-5-phenylthio-7-azido-1-azabicyclo[4,2,0]oct-2-en-8-on-2-carboxylate A' (which is the less polar isomer obtained as in Example 11-4) is dissolved in 8 ml of methanol and 0.8 ml of benzene and 140 mg (0.655 mmole) of aqueous sodium periodate is added thereto. The mixture is stirred at room temperature for 60 hours. To the reaction mixture, water is added and then 15 ml of methylene chloride is added for extraction. The methylene chloride solution is dried over anhydrous magnesium sulfate and concentrated under reduced pressure to obtain 105 mg of an oily product. Based on the following data, the product is identified as t-butyl (±)-cis-5-phenylsulfinyl-7-azido-1-azabicyclo[4,2,0]-oct-2-en-8-on-2-carboxylate A.

IR $\nu_{max}^{CHCl_3}$ (cm$^{-1}$): 2130, 1790, 1725, 1640, 1050

NMR $\delta$(CDCl$_3$)ppm: 7.55(5H, m), 6.30(1H, m), 5.27(0.5H, d, J=5 Hz), 4.78(0.5H, d, J=5 Hz), 4.07(1H, dd, J=5, 10 Hz), 2.40-3.00(2H, m)

(6) Preparation of t-butyl (±)-cis-5-phenylsulfinyl-7-azido-1-azabicyclo[4,2,0]oct-2-en-8-on-2-carboxylate B In this Example, 1.03 g (2.77 mmoles) of t-butyl (±)-cis-5-phenylthio-7-azido-1-azabicyclo[4,2,0]oct-2-en-8-on-2-carboxylate B' (which is the more polar isomer and obtained as in Example 11-4) is dissolved in 80 ml of methanol followed by the addition of 1.3 g (6.1 mmoles) of aqueous sodium periodate in 20 ml of water and the mixture is stirred at room temperature for 78 hours. After adding 80 ml of water, the reaction mixture is extracted twice with 150 ml of chloroform, dried with sodium sulfate and distilled under reduced pressure to obtain 1.00 g of the desired compound. Yield 93.1%.

IR $\nu_{max}^{CHCl_3}$ (cm$^{-1}$): 2120, 1790, 1720, 1630, 1030

Other variations and embodiments of the above invention will be apparent to those skilled in the art. This invention is not to be limited except as set forth in the following claims.

What is claimed is:

1. Cephalosporin analogs represented by the formula

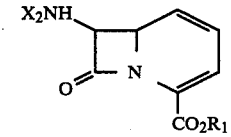

wherein $X_2$ represents an acyl group represented by the formula $X^1CO$ wherein $X^1$ represents:

(a) cyanomethyl group or a group represented by the formula

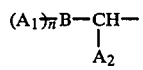

wherein B represents an unsaturated six membered carbo-cycle which is selected from cyclohexenyl group, cyclohexadienyl group and phenyl group or a five or six membered heterocycle selected from the groups consisting of furyl group, thienyl group, pyrrolyl group, thiazolyl group, oxazolyl group, isothiazolyl group, isoxazolyl group, imidazolyl group, pyrazolyl group, triazolyl group, tetrazolyl groups, pyridinyl group, pyrimidinyl group, pyrazinyl group, pyridazinyl group, triazinyl group and 5,6-dihydro-1,4-dithiin-2-yl group, $A_1$ represents a substituent which is selected from hydrogen atom, hydroxyl group, a lower alkoxy group having 1 to 4 carbon atoms, a halo group, nitro group, amino group, aminomethyl group, methylsulfonamido group and a lower acyloxy group having 2 to 4 carbon atoms selected from the groups consisting of acetyloxy group, propyloxy group and butyloxy group, n is a number from 0 to 5, and $A_2$ represents hydrogen atom, amino group, hydroxyl group, carboxyl group or sulfoxyl group, (b) a group represented by the formula

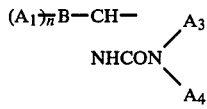

wherein A, B and n have the same significance as defined above, $A_3$ and $A_4$ are the same or different and represent (1) hydrogen atom, a lower alkyl group having 1 to 4 carbon atoms, (2) a group represented by the formula

wherein $A_5$ represents a lower alkyl group having 1 to 4 carbon atoms or (3) a group represented by the formula

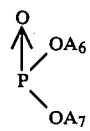

wherein $A_6$ and $A_7$ are the same or different and represent hydrogen atom, a lower alkyl group having 1 to 4 carbon atoms or an alkali metal or

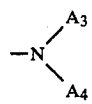

also represents a group represented by the formula

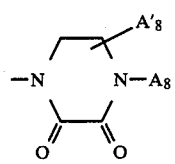

wherein $A_8$ and $A'_8$ are the same or different and represent hydrogen atom or a lower alkyl group having 1 to 4 carbon atoms or a group represented by the formula

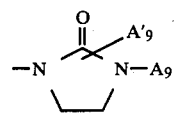

wherein $A_9$ represents hydrogen atom, a lower alkyl group having 1 to 4 carbon atoms, methylsulfonyl group or furfurylideneimimo group and $A'_9$ represents hydrogen atom or a lower alkyl group having 1 to 4 carbon atoms, (c) a group represented by the formula

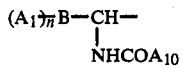
NHCOA$_{10}$ wherein $A_1$, B and n have the same significance as defined above, and $A_{10}$ represents an aryl group or a mono-, bi- or tricyclic hetercycle(s) selected from a group represented by the formula

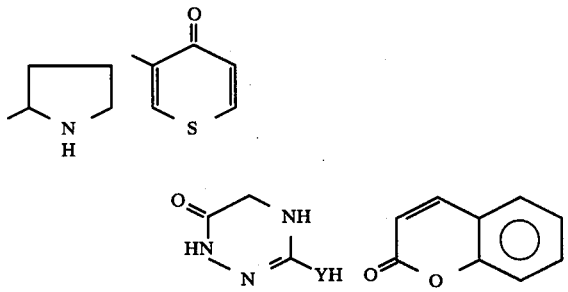

wherein Y is an oxygen or sulfur atom and

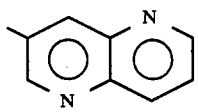

(d) a group represented by the formula

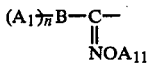
NOA$_{11}$ wherein $A_1$, B and n have the same significance as defined above and $A_{11}$ represents hydrogen atom, a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms selected from the groups consisting of cyclopropyl group, cyclobutyl group and cyclohexyl group, those groups being unsubstituted or substituted with substituents selected from carboxyl group, cyano group, a halo group, carbamoyl group and a lower alkyloxycarbonyl group having 1 to 4 carbon atoms, (e) a group represented by the formula

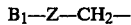

wherein $B_1$ represents trifluoromethyl group, cyanomethyl group, a group represented by the formula $(A_1)_nB$- wherein $A_1$, n and B have the same significance as defined above and Z represents oxygen atom or sulfur atom, $R_1$ represents hydrogen atom or a protecting group of carboxylic acid, which is selected from an alkyl group having 1 to 5 carbon atoms, a halogenated alkyl group having 1 to 5 carbon atoms, an aryl methyl group having 7 to 20 carbon atoms which may be substituted on the phenyl ring, a substituted silyl group, wherein the substituent is selected from a lower alkyl group having 1 to 5 carbon atoms and an aryl group having 6 to 10 carbon atoms and a group enzymatically or nonenzymatically readily eliminable in vivo selected from groups represented by the formula

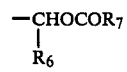

wherein $R_6$ represents a hydrogen atom or a lower alkyl group having 1 to 6 carbon atoms, and $R_7$ represents a lower alkyl group having 1 to 6 carbon atoms, a lower alkoxy group having 1 to 6 carbon atoms or a phenyl group and the pharmaceutically acceptable salts thereof.

2. The compounds of claim 1, wherein hydrogens at the 6- and 7-positions in the formula have "cis" configuration.

3. The compounds of claims 1 or 2, wherein $R_1$ is a hydrogen atom.

4. The compounds of claims 1 or 2, wherein $R_1$ is an alkyl group having 1 to 5 carbon atoms.

5. The compounds of claim 4, wherein $R_1$ is a t-butyl group.

6. The compounds of claims 1 or 2, wherein the aryl methyl group is benzyl group, diphenyl methyl group or triphenylmethyl group.

7. The compounds of claim 1 wherein B is a phenyl group.

8. The compounds of claim 1, wherein B is thienyl group, furyl group, pyrrolyl group, thiazolyl group, oxazolyl group, isothiazolyl group, isoxazolyl group, imidazolyl group, pyrazolyl group, triazolyl group, tetrazolyl group, pyridinyl group, pyrimidinyl group, pyrazinyl group, pyridazinyl group, triazinyl group or 5,6-dihydro-1,4-dithin-2-yl group.

9. The compounds of claim 8 wherein B is a furyl group.

10. The compounds of claim 8 wherein B is a thiazolyl group.

11. The compounds of claim 7 wherein $A_1$ is a hydrogen atom.

12. The compounds of claim 7 wherein $A_1$ is a group which is selected from hydroxyl group, halo group, amino group, aminomethyl group and methylsulfonamido group and n is 1 or 2.

13. The compounds of claim 7, wherein $A_1$ is an hydroxyl group and n is 1.

14. The compounds of claim 10 wherein $A_1$ is an amino group and n is 1.

15. The compounds of claim 7 wherein $A_2$ is a hydrogen atom.

16. The compounds of claim 7 wherein $A_2$ is an hydroxyl group.

17. The compounds of claim 7 wherein $A_2$ is an amino group.

18. The compounds of claim 7 wherein the group represented by the formula

is a group represented by the formula

[Structure: piperazine-2,3-dione with A'8 and N-A8]

19. The compounds of claim 18 wherein $A_8$ is an ethyl group and $A'_8$ is a hydrogen atom.

20. The compounds of claim 7 wherein the group represented by the formula $$-N\begin{matrix}A_3\\A_4\end{matrix}$$

is a group represented by the formula

[Structure: imidazolidinone ring with N-A9 and A'9]

21. The compounds of claim 20, wherein $A'_9$ is a hydrogen atom and $A_9$ is a methylsulfonyl group or a furfurylideneimino group.

22. The compounds, of claim 7 wherein $A_{10}$ is (1) a mono-, bi- or tricyclic heterocycle selected from the group represented by the formulae:

[Two structures: a pyrrolidine-fused thiopyranone; and an acyl-aminopyrimidine with YH]

wherein Y is oxygen or sulfur atom, (2) a substituted or unsubstituted 2-oxo-2H-1-benzopyran-3-yl group and (3) a substituted or unsubstituted naphthyridinyl group which substituent(s) is selected from those groups represented by $A_1$.

23. The compounds of claim 22, wherein the substituted naphthyridinyl group is the group represented by the formula:

[Structure: hydroxynaphthyridine]

24. The compounds of claim 7 wherein $A_{11}$ is a hydrogen atom.

25. The compounds of claim 7 wherein $A_{11}$ is a substituted or unsubstituted alkyl group having 1 to 6 carbon atoms.

26. The compounds of claim 25 wherein $A_{11}$ is a methyl group.

27. The compounds of claim 7 wherein $A_{11}$ is a substituted or unsubstituted alkenyl group having 2 to 4 carbon atoms.

28. The compounds of claim 27 wherein $A_{11}$ is a vinyl group or allyl group.

29. The compounds of claim 24 wherein the group represented by the general formula $-OA_{11}$ has "syn" configuration.

30. ($\pm$)-cis-7-[2-(thiophene-2-yl)acetylamino]-1-azabicyclo[4,2,0]oct-2,4-diene-8-on-2-carboxylic acid.

31. ($\pm$)-cis-7-[2-(2-amino-4-thiazolyl)-2-antimethoxyiminoacetamido]-1-azabicyclo[4,2,0]oct-2,4-diene-8-on-2-carboxylic acid.

32. ($\pm$)-cis-7-[2-(N-chloroacetyl-2-amino-4-thiazolyl)-2-syn-methoxyiminoacetamido]-1-azabicyclo[4,2,0]oct-2,4-diene-8-on-2-carboxylic acid.

33. ($\pm$)-cis-7-[2-(2-amino-4-thiazolyl)-2-syn-methoxyiminoacetamido]-1-azabicyclo[4,2,0]oct-2,4-diene-8-on-2-carboxylic acid.

* * * * *